# (12) United States Patent
Kalapudas et al.

(10) Patent No.: US 6,891,070 B2
(45) Date of Patent: May 10, 2005

(54) METHOD FOR THE PREPARATION OF 2-{2-[4-(4-CHLORO-1,2-DIPHENYLBUT-1-ENYL)PHENOXY]ETHOXY}ETHANOL AND ITS ISOMERS

(75) Inventors: Arja Kalapudas, Oulu (FI); Marja Södervall, Oulu (FI)

(73) Assignee: Hormos Medical Corporation, Turku (FI)

( * ) Notice: Subject to any disclaimer, the term of this patent is extended or adjusted under 35 U.S.C. 154(b) by 27 days.

(21) Appl. No.: 10/474,717

(22) PCT Filed: Mar. 21, 2002

(86) PCT No.: PCT/FI02/00235

§ 371 (c)(1),
(2), (4) Date: Oct. 10, 2003

(87) PCT Pub. No.: WO02/090305

PCT Pub. Date: Nov. 14, 2002

(65) Prior Publication Data

US 2004/0116538 A1 Jun. 17, 2004

(30) Foreign Application Priority Data

May 4, 2001 (FI) .............................................. 20010927

(51) Int. Cl.⁷ .......................... C07C 41/01; C07C 41/14; C07C 43/215; C07C 43/225; C07C 43/23

(52) U.S. Cl. ........................ 568/609; 568/610; 568/641
(58) Field of Search ................................. 568/609, 610, 568/641, 333

(56) References Cited

U.S. PATENT DOCUMENTS

| 5,491,173 A | 2/1996 | Toivola et al. ............... 514/648 |
| 6,576,645 B1 | 6/2003 | Sodervall et al. ........... 514/317 |

FOREIGN PATENT DOCUMENTS

WO     WO 01/36360     5/2001     ........... C07C/43/23

OTHER PUBLICATIONS

Ferguson et al., Alkali Metal Ion Mediated Cyclization of 4,4'-(3,6-dioxaocta-1,8-diyloxy)-bis(benzophenone), Tetrahedron Letters, Jun. 1993, vol. 34, No. 23, pp. 3719-3722.*

* cited by examiner

*Primary Examiner*—Rosalynd Keys
(74) *Attorney, Agent, or Firm*—James C. Lydon

(57) ABSTRACT

A new method for the preparation of a selective estrogen receptor modulator and its isomers. Also disclosed is the preparation of new intermediates and their use in the preparation of the selective estrogen receptor modulator.

8 Claims, No Drawings

METHOD FOR THE PREPARATION OF 2-{2-[4-(4-CHLORO-1,2-DIPHENYLBUT-1-ENYL) PHENOXY]ETHOXY}ETHANOL AND ITS ISOMERS

This application is a U.S. National Stage of International application PCT/FI02/00235, filed Mar. 21, 2002.

FIELD OF THE INVENTION

This invention relates to a new method for the preparation of 2-{2-[4-(4-chloro-1,2-diphenylbut-1-enyl)phenoxy]ethoxy}ethanol (illustrated by formula I below) and its isomers as well as new intermediates prepared and further used in the method.

BACKGROUND OF THE INVENTION

The publications and other materials used herein to illuminate the background of the invention, and in particular, cases to provide additional details respecting the practice, are incorporated by reference.

Estrogens are increasingly used for the treatment of climacteric symptoms in women. Estrogens are shown to be beneficial also in the prevention of Alzheimer's disease (Henderson, 1997) and in the lowering of LDL-cholesterol values and thus preventing cardiovascular diseases (Grodstein & Stampfer, 1998). However, estrogen use increases the risk of uterine and breast cancers (Lobo, 1995). New therapies which would have the benefits of estrogens, but not the carcinogenic risks are requested. Selective estrogen receptor modulators (SERMs) have been developed to fulfill these requirements (Macgregor & Jordan, 1998). However, the presently used SERMs have properties which are far from optimal.

The international patent application PCT/FI00/00946 relates to a novel group of SERMs which are tissue-specific estrogens and which can be used in women in the treatment of climacteric symptoms, osteoporosis, Alzheimer's disease and/or cardiovascular diseases without the carcinogenic risk. Certain compounds can be given to men to protect them against osteoporosis, cardiovascular diseases and Alzheimer's disease without estrogenic adverse events (gynecomastia, decreased libido etc.). Of the compounds claimed in said international patent application, the compound 2-{2-[4-(4-chloro-1,2-diphenylbut-1-enyl)phenoxy] ethoxy}ethanol (referred to as compound No. 19 in said patent application) has shown a very interesting hormonal profile suggesting that it will be especially valuable for treating disorders in men, particularly for preventing osteoporosis in men.

SUMMARY OF THE INVENTION

According to one aspect, this invention concerns a new method for the preparation of the compound (I), which is therapeutically useful as a selective estrogen receptor modulator,

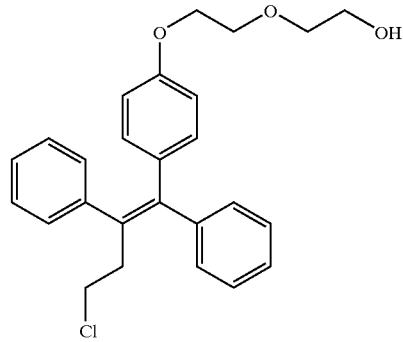

wherein a) a compound of formula (II)

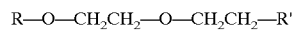

where R is a protecting group and R' is halogen, preferably Cl; —OSO$_2$CH$_3$ or tosylate, is reacted with 4-hydroxybenzophenone to give a compound of formula (III),

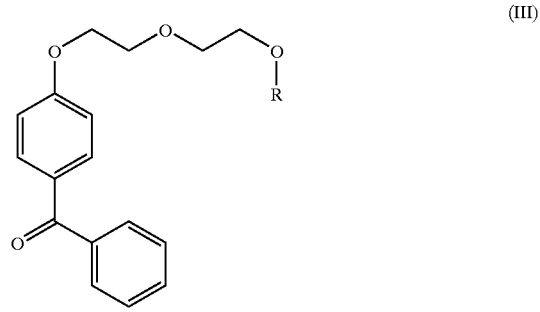

b) the compound (III) is reacted with cinnamaldehyde and LiAlH$_4$ in a suitable solvent to give a compound of formula (IV)

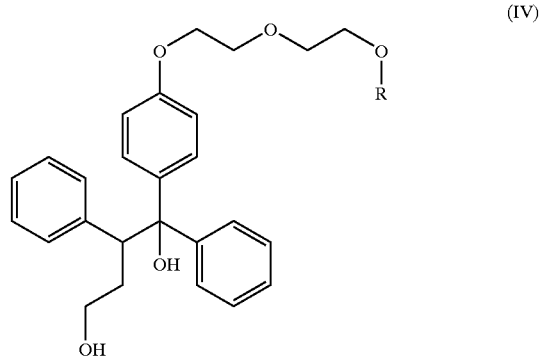

c) the compound (IV) is reacted with thionyl chloride in a suitable solvent to give a compound of formula (V)

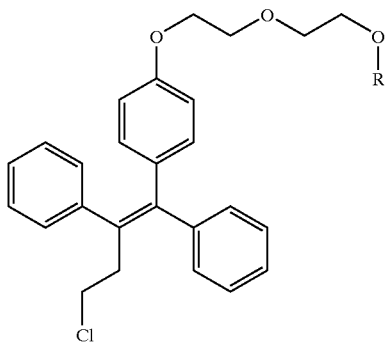

(V)

and d) the protecting group R is removed from the compound (V) to give the compound of formula (I).

According to further aspects, this invention concerns also any of the intermediates of formulas (III), (IV) and (V).

DETAILED DESCRIPTION OF THE INVENTION

The formulas shown in this text shall be understood to cover also isomers and mixtures of isomers.

The protection group R as shown in formulas (II), (III), (IV) and (V) shall preferably be a protection group which has good stability (i.e. it will not undergo unintentional cleavage) in both acidic and alkaline conditions, such as allyl, benzyl or substituted benzyl, preferable benzyl.

The reaction in step a) is preferably carried out as a phase-transfer catalysis in the presence of a quaternary ammonium salt. Alternatively, the sodium salt of 4-hydroxybenzophenone can be reacted with the compound of formula (II) in DMF.

The solvent used in step b) is preferably tetrahydrofuran. As examples of other useful alternatives can be mentioned ethers e.g. diethyl ether and dimethoxyethane.

The solvent to be used in step c) shall be able to dissolve the compound (IV) but not to react with the thionyl chloride. As suitable solvents can be mentioned toluene and dichloromethane.

The removal of the protecting group R in step d) is preferably carried out by hydrogenation with metal catalyst in appropriate solvent or by selective cleavage of nonaromatic ethers with Zn/Acyl chloride.

The invention will be illuminated by the following non-restrictive Example.

EXAMPLE a) [2-(2-chloroethoxy)ethoxymethyl]benzene is prepared from benzyl bromide and 2-(2-chloroethoxy) ethanol by the method described in literature (Bessodes, 1996).

b) {4-[2-(2-Benzyloxyethoxy)ethoxy]phenyl}phenylmethanone

The mixture of 4-hydroxybenzophenone (16.7 g, 84.7 mmol) and 48% aqueous sodium hydroxide solution (170 ml) is heated to 80° C. Tetrabutylammonium bromide (TBABr) (1.6 g, 5.1 mmol) is added and the mixture is heated to 90° C. [2-(2-Chloroethoxy)ethoxymethyl]benzene (18. g, 84.7 mmol) is added to the mixture during 15 min and the stirring is continued for additional 3.5 h at 115–120° C. Then the mixture is cooled to 70° C. and 170 ml of water and 170 ml of toluene are added to the reaction mixture and stirring is continued for 5 min. The layers are separated and the aqueous phase is extracted twice with 50 ml of toluene. The organic phases are combined and washed with water, dried with sodium sulphate and evaporated to dryness. Yield 31.2 g.

Another method to prepare {4-[2-(2-benzyloxyethoxy)ethoxy]phenyl}phenylmethanone is the reaction of 2-(2-benzyloxyethoxy)ethyl mesylate with 4-hydroxybenzophenone in PTC-conditions.

$^1$H NMR (CDCl$_3$): 3.64–3.69 (m, 2H), 3.74–3.79 (m, 2H), 3.90 (dist.t, 2H), 4.22 (dist.t, 2H), 4.58 (s, 2H), 6.98 (d, 2H), 7.28–7.62 (m, 8H), 7.75 (td, 2H), 7.81 (d, 2H).

c) 1-{4-[2-(2-Benzyloxyethoxy)ethoxy]phenyl}-1,2-diphenyl-butane-1,4-diol

Lithium aluminum hydride (1.08 g, 28.6 mmol) is added into dry tetrahydrofuran (60 ml) under nitrogen atmosphere. Cinnamaldehyde (6.65 g, 50 mmol) in dry tetrahydrofuran (16 ml) is added at 24–28° C. The reaction mixture is stirred at ambient temperature for 1 h. {4-[2-(2-Benzyloxyethoxy)ethoxy]phenyl}-phenyl-methanone (14.0 g, 37 mmol) in dry tetrahydrofuran (16 ml) is added at 50–55° C. The reaction mixture is stirred at 60° C. for 3 h. Most of tetrahydrofuran is evaporated. Toluene (70 ml) and 2 M aqueous hydrogen chloride (50 ml) are added. The mixture is stirred for 5 min and the aqueous layer is separated and extracted with toluene (30 ml). The toluene layers are combined and washed with 2M HCl and water, dried and evaporated. The product is crystallized from isopropanol as a mixture of stereoisomers (8.8 g, 50%).

$^1$H NMR (CDCl$_3$): 1.75–2.10 (m, 2H), 3.20–4.16 (m, 10H), 4.52 and 4.55 (2s, together 2H), 6.61 and 6.88 (2d, together 2H), 6.95–7.39 (m, 15H), 7.49 and 7.57 (2d, together 2H).

d) Z-1-{4-[2-(2-Benzyloxyethoxy)ethoxy]phenyl}-4-chloro-1,2-diphenyl-but-1-ene

1-{4-[2-(2-Benzyloxy-ethoxy)ethoxy]phenyl}-1,2-diphenyl-butane-1,4-diol (10.0 g, 19.5 mmol) is dissolved in toluene (50 ml). Triethylamine (2.17 g, 21.4 mmol) is added to the solution and the mixture is cooled to −10° C. Thionyl chloride (6.9 g, 58.5 mmol) is added to the mixture at −10–±0° C. The mixture is stirred for 1 hour at 0–5° C., warmed up to 70° C. and stirred at this temperature for 4 hours. Solvent is evaporated, the residue is dissolved to toluene, washed three times with 1M HCl solution and twice with water. The Z-isomer of the product is crystallized from isopropanol-ethyl acetate. Yield 3.0 g. The filtrate is purified by flash chromatography to give E-isomer.

Z-isomer: $^1$H NMR (CDCl$_3$): 2.91 (t, 2H), 3.41 (t, 2H), 3.55–3.85 (m, 6H), 3.99 (dist.t, 2H), 4.54 (s, 2H), 6.40 (s, 1H), 6.56 (d, 2H), 6.77 (d, 2H), 7.10–7.50 (m, 15H)

E-isomer: $^1$H NMR (CDCl$_3$): 2.97 (t, 2H), 3.43 (t, 2H), 3.65–3.82 (m, 4H), 3.88 (dist.t, 2H), 4.15 (dist.t, 2H), 4.58 (s, 2H), 6.86–7.45 (m, 19H)

e) 2-{2-[4-(4-Chloro-1,2-diphenyl-but-1-enyl)phenoxy]ethoxy}ethanol:

Z-1-{4-[2-(2-Benzyloxy-ethoxy)ethoxy]phenyl}-4-chloro-1,2-diphenyl-but-1-ene (3.8 g, 7.4 mmol) is dissolved in ethyl acetate under nitrogen atmosphere, Zn powder (0.12 g, 1.85 mmol) and acetyl chloride (1.27 g, 16.3 mmol) are added and the mixture is stirred at 50° C. for 3 h (Bhar, 1995). The reaction mixture is cooled to room temperature, water (10 ml) is added and stirring is continued for additional 10 min. The aqueous layer is separated and the organic phase is washed with 1 M aqueous hydrogen chloride solution and with water. Ethyl acetate is evaporated and the residue is dissolved in methanol (16 ml) and water (4 ml). The acetate ester of the product is hydrolysed by making the mixture alkaline with sodium hydroxide (1 g) and stirring the mixture at room temperature for 1 h. Methanol is evaporated, water is added and the residue is extracted in ethyl acetate and washed with 1 M hydrogen chloride solution and with water. Ethyl acetate is evaporated and the residue is dissolved in toluene (25 ml), silica gel (0.25 g) is added and mixture is stirred for 15 min. Toluene is filtered and evaporated to dryness.

The residue is crystallised from heptane-ethyl acetate (2:1). The yield is 71%.

Z-isomer: $^1$H NMR (CDCl$_3$): 2.92 (t, 2H), 3.41 (t, 2H), 3.58–3.63 (m, 2H), 3.69–3.80 (m, 4H), 3.96–4.01 (m, 2H), 6.56 (d, 2H), 6.78 (d, 2H), 7.10–7.40 (m, 10H).

E-2-{2-[4-(4-Chloro-1,2-diphenyl-but-1-enyl)phenoxy]ethoxy}ethanol is prepared analogously starting from E-1-{4-[2-(2-benzyloxy-ethoxy)ethoxy]phenyl}-4-chloro-1,2-diphenyl-but-1-ene. The product is purified by flash chromatography with toluene-methanol (10:0.5) as eluent.

E-isomer: $^1$H NMR (CDCl$_3$): 2.97 (t, 2H), 3.43 (t, 2H), 3.65–3.79 (m, 4H), 3.85–3.90 (m, 2H), 4.13–4.17 (m, 2H), 6.85–7.25 (m, 2H).

Debenzylation of 1-{4-[2-(2-benzyloxy-ethoxy)ethoxy]phenyl}-4-chloro-1,2-diphenyl-but-1-ene is also carried out by hydrogenation with Pd on carbon as a catalyst in ethyl acetate-ethanol solution at room temperature.

It will be appreciated that the present invention can be incorporated in the form of a variety of embodiments, only a few of which are disclosed herein. It will be apparent for the expert skilled in the field that other embodiments exist and do not depart from the spirit of the invention. Thus, the described embodiments are illustrative and should not be construed as restrictive.

References

Grodstein F, Stampfer M J: Estrogen for women at varying risk of coronary disease. Maturitas 30: 19–26, 1998.

Henderson V W: Estrogen, cognition, and a woman's risk of Alzheimer's disease. Am J Med 103(3A): 11S–18S, 1997.

Lobo R A: Benefits and risks of estrogen replacement therapy. Am J Obstet Gynecol 173:982–990, 1995.

Macgregor J I, Jordan V C: Basic guide to the mechanism of antiestrogen action. Pharmacol Rev 50:151–196, 1998.

Bessodes et al., Synlett, 1996, 1119–20.

Bhar S., Ranu B. C., J. Org. Chem. 1995, 60, 745–47.

What is claimed is:

1. Method for the preparation of the compound (I), which is therapeutically useful as a selective estrogen receptor modulator,

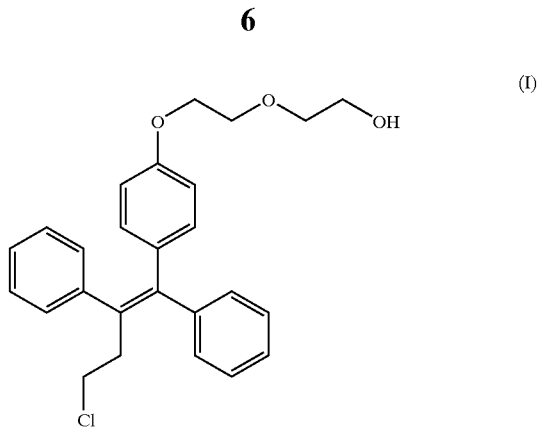

(I)

wherein a) a compound of formula (II)

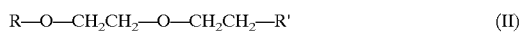

(II)

where R is a protecting group and R' is halogen, —OSO$_2$CH$_3$ or tosylate, is reacted with 4-hydroxybenzophenone to give a compound of formula (III),

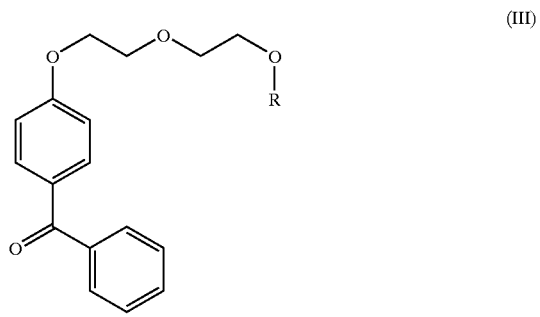

(III)

b) the compound (III) is reacted with cinnamaldehyde and LiAlH$_4$ in a suitable solvent to give a compound of formula (IV)

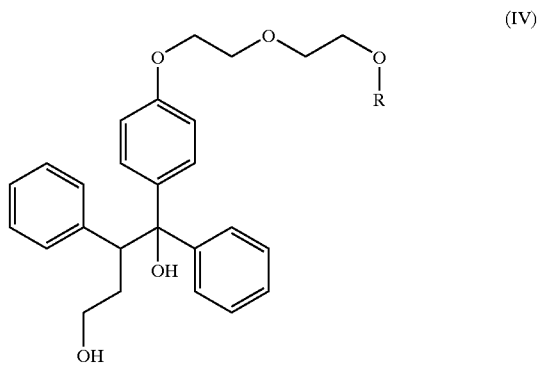

(IV)

c) the compound (IV) is reacted with thionyl chloride in a suitable solvent to give a compound of formula (V)

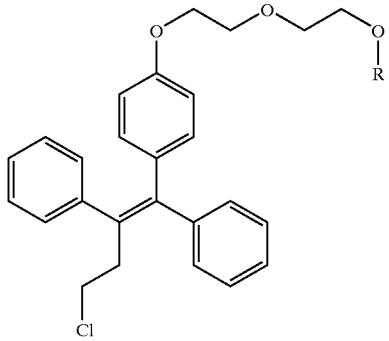

and d) the protecting group R is removed from the compound (V) to give the compound of formula (I).

2. The method of claim 1, wherein the protecting group R is allyl, benzyl or substituted benzyl.

3. The method of claim 1, wherein the reaction in step a) is carried out as a phase-transfer catalysis, and the solvent in step b) is tetrahydrofuran and the solvent in step c) is toluene.

4. The method of claim 1, wherein the removal of the protecting group in step d) is carried out i) by hydrogenation with metal catalyst in appropriate solvent or ii) by selective cleavage of a nonaromatic ether with Zn/Acyl chloride.

5. A compound of formula (IV)

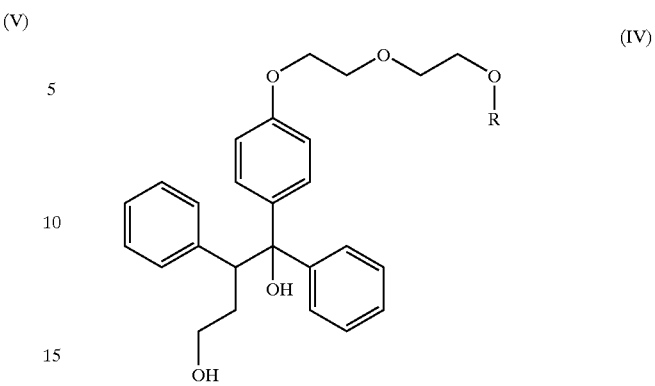

wherein R is a protecting group.

6. A compound of formula (V)

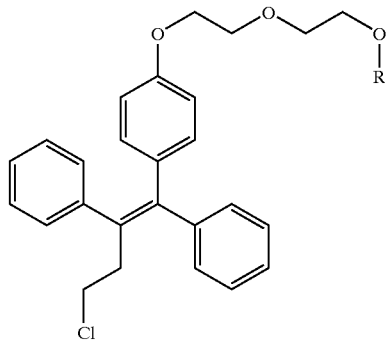

wherein R is allyl, benzyl or substituted benzyl.

7. The compound of (V) claim 6, wherein R is benzyl.

8. The method of claim 1, wherein R' is Cl.

* * * * *